United States Patent [19]

Fergason et al.

[11] Patent Number: 5,377,032
[45] Date of Patent: Dec. 27, 1994

[54] ELECTRO-OPTIC LIGHT SHUTTER AND FRAME ASSEMBLY WITH INTEGRATED SWITCHING MECHANISM

[75] Inventors: Jeffrey K. Fergason, Menlo Park; John D. Fergason, Mountainview, both of Calif.

[73] Assignee: OSD Envizion Company, Menlo Park, Calif.

[21] Appl. No.: 13,966

[22] Filed: Feb. 5, 1993

[51] Int. Cl.⁵ .............................. B23K 9/32; A61F 9/06
[52] U.S. Cl. ..................................... 359/62; 359/58; 359/63; 359/85; 2/8; 2/431
[58] Field of Search ............... 2/8, 431; 219/147; 250/205; 359/58, 62, 63, 85

[56] References Cited

U.S. PATENT DOCUMENTS

| | | | |
|---|---|---|---|
| Re. 29,684 | 6/1978 | Gordon | 219/147 |
| 4,039,254 | 8/1977 | Harsch | 350/160 |
| 4,039,803 | 8/1977 | Harsch | 359/62 X |
| 4,071,912 | 2/1978 | Bubmiger | 2/8 |
| 4,237,557 | 12/1980 | Gordon | 2/8 |
| 4,728,173 | 3/1988 | Toth | 350/332 |
| 4,863,244 | 9/1989 | Fuerthbauer et al. | 350/332 |
| 4,901,074 | 2/1990 | Sinn | 200/5 A X |
| 5,015,086 | 5/1991 | Okaue et al. | 351/44 |
| 5,184,156 | 2/1993 | Black et al. | 351/158 |
| 5,208,688 | 5/1993 | Fergason | 359/53 |
| 5,224,219 | 7/1993 | Edwards | 2/8 |

FOREIGN PATENT DOCUMENTS

| | | | |
|---|---|---|---|
| 0157744 | 10/1985 | European Pat. Off. | G02F 1/13 |
| 0335056 | 10/1989 | European Pat. Off. | G02F 1/13 |
| 0349665 | 1/1990 | European Pat. Off. | A61F 9/06 |
| 55-92276 | 7/1980 | Japan | B23K 9/32 |
| 7608690 | 2/1979 | Sweden | G02B 5/20 |
| WO9014809 | 12/1990 | WIPO | A61F 9/06 |

OTHER PUBLICATIONS

U.S. Patent Application Ser. No. 07/943,994 to John D. Fergason filed Sep. 11, 1992.

*Primary Examiner*—Eugene R. LaRoche
*Assistant Examiner*—Son Mai
*Attorney, Agent, or Firm*—Renner, Otto, Boisselle & Sklar

[57] ABSTRACT

A frame assembly for a light shutter including a frame structure for enclosing an electro-optic shutter assembly, the frame structure having a front surface which can be positioned opposite a cover lens, and a switch for controlling an operation mode of the electro-optic shutter assembly, the switch being mounted on the front surface whereby pressure applied to the cover lens activates the switch. The frame assembly can be inserted and used in a welding helmet or other protective eyewear having a standard sized lens aperture.

34 Claims, 2 Drawing Sheets

ELECTRO-OPTIC LIGHT SHUTTER AND FRAME ASSEMBLY WITH INTEGRATED SWITCHING MECHANISM

TECHNICAL FIELD

The present invention relates generally, as is indicated, to an electro-optic light shutter and, more particularly, to a light shutter frame assembly which includes an integrated switching mechanism for controlling an operating mode of the light shutter.

BACKGROUND

The present invention is described below with respect to an electro-optic liquid crystal shutter. It will be appreciated, though, that features of the invention may be utilized with shutters formed of materials other than liquid crystal and also may be utilized with devices other than shutters. A shutter, as is used herein, refers to a device for controlling intensity of electromagnetic energy or electromagnetic radiation that is being transmitted through the shutter. In the preferred embodiment described in detail below, such electromagnetic energy is in the form of light and more preferably is in the form of light (i.e., electromagnetic energy) that is in the visible spectrum as well as in the various infrared spectra and ultraviolet spectra, all collectively referred to as light below. Such control may be by way of graduated or analog control or intensity of transmitted light preferably without detrimentally affecting the image characteristics of such light. Such control also may be digital, i.e., on, off, and specific intermediate levels of transmission or intensity, etc.

A problem associated with existing electro-optic light shutters used as part of protective eye wear such as goggles, welding helmets, or the like, is that the driver circuit for driving the shutter can occupy a relatively large amount of space. As a result, the light shutter and driver circuit may be too large to fit in the lens aperture of the protective eye wear. For example, welding helmets usually are manufactured with a standard sized lens aperture. A welder can insert a variety of standard sized protective cover lenses and/or filters such as a shade filter or ultraviolet filter in the lens aperture as may be desired for eye protection under a particular condition, e.g., depending on the type of welding materials being welded, brightness of ambient light, etc. The lens aperture is standard sized so that the welder can select and insert a desired type of lens or filter based on the particular type of welding application. The lenses and filters are commercially available in the same standard sizes so the welder can change easily amongst the different types of lenses or filters.

An exemplary welding helmet having a standard size lens aperture (approx. 2 inches by 4.25 inches) is sold by Sellstrom as Model No. 295 11. An exemplary standard size lens is a "100% Cast Resin Welders Plastic Cover Lens" available from Wesco in Redwood City, Calif. U.S.A. Such a lens is manufactured, for example, under such standards as Federal Spec. GGG-H-211C and ANSI Std. Z87. Also, it will be appreciated that protective cover lenses, lenses and filters, as referred to herein, are referred to collectively as both lenses and cover lenses and are intended to be equivalent at least in the context of the invention.

Conventional electro-optic shutters are typically too large to be inserted into a standard size lens aperture. As a result, the standard size lens aperture in the welding helmet must be enlarged and the standard size lenses no longer fit in the aperture. Alternatively, the driver circuit for the shutter must be positioned in the helmet somewhere other than the lens aperture. This requires that the helmet be custom designed or modified to accommodate the driver circuit, resulting in additional expense and/or lost time.

Furthermore, a cover lens is useful for protecting the light shutter in addition to the eyes of the user. For example, the cover lens protects the light shutter from damage or dirt due to contact with fingers, etc. Also, sputtering, splash, spray, flying particles, etc., which may occur during welding, can damage the light shutter. Typically, therefore, a cover lens is included in the welding helmet lens aperture in front of the light shutter to protect the light shutter from damage due to such sputtering, etc.

In the event the cover lens itself becomes damaged, however, it is necessary to replace the cover lens. Therefore, again it is highly desirable that the welder be able to replace an existing cover lens with a standard size cover lens. If the light shutter requires a non-standard size cover lens, this may result in additional expense associated with nonstandard sized parts. Alternatively, production time can be lost and/or undesirable costs incurred as a result of having to modifying a standard size cover lens to tit the nonstandard sized shutter/aperture.

Still another drawback associated with conventional light shutters used as part of welding helmets or other protective eye gear is that the switching mechanism for turning the light shutter on and off is difficult to access and/or requires modification of the helmet and other standard size parts. For example, a conventional light shutter for a welding helmet includes an on/off switch on the light shutter frame assembly on the inside of the helmet. This requires that the welder take off the helmet in order to turn the shutter on and off. Obviously, this can be very inconvenient to the welder. Furthermore, some of such light shutters require a non-standard size cover lens so as to provide access to the on/off switch from the inside of the helmet.

In view of the aforementioned shortcomings associated with existing light shutters, there is a need for a light shutter including a drive circuit which can be inserted in a standard sized aperture of a welding helmet or the like. There is a need for such a light shutter which can be used with standard size cover plates to protect the light shutter and the eyes of a user from being damaged. Further, there is a need for such a light shutter with a switching mechanism for powering on and off the light shutter which can be easily activated. In particular, there is a need for a switching mechanism which does not require customization of the standard components associated with a welding helmet or the like, e.g., the helmet assembly or cover plates.

As will be appreciated based on the following detailed description, an exemplary liquid crystal shutter with which the invention may be utilized is disclosed in U.S. Pat. Nos. 4,385,806, 4,540,243, 4,582,396 and Re. 32,521. An example of such shutter includes a pair of linear (plane) polarizers, one being used as an input polarizer and the other as an output analyzer, and a variable liquid crystal optical retarder between the two polarizers. By changing the electric field applied to liquid crystal in the retarder, the plane of polarization (or relationships of the axes of elliptically polarized light) of the light transmitted through the retarder can be changed; and the intensity of light transmitted through the analyzer will be a function of the polarization direction (characteristics) of the light transmitted through the retarder.

A shutter system which may employ such an exemplary liquid crystal shutter is disclosed in copending, commonly owned U.S. Pat. application Ser. No. 07/653,661 filed Feb. 8, 1991, for "Eye Protection System For Welding Helmets And The Like".

An exemplary driver circuit with which the present invention can be utilized is described in commonly assigned, co-pending U.S. Pat. application Ser. No. 07/674,850 filed Mar. 25, 1991, for "Liquid Crystal Lens Driver Electronics for Eye Protection and High Speed Shuttenng", and U.S. Pat. application Ser. No. 07/814,372 filed Dec. 26, 1991, for "Welding Arc Light Detector for Use with Electronic Eye Protection and High Speed Shuttering." The disclosures of the above patents and patent application are incorporated herein in their entireties by this express reference thereto.

BRIEF SUMMARY OF THE INVENTION

The present invention overcomes the above-mentioned shortcomings associated with existing light shutters used for eye protection. The various objects, features, aspects and advantages of the present invention will become more apparent as the following description proceeds. It will be appreciated that while a preferred embodiment of the invention is described herein, the scope of the invention is to be determined by the claims and equivalents thereof.

The present invention is particularly useful for eye protection wherein the light shutter is to be used with other components having standard dimensions such as a helmet or goggle assembly or in another device, if desired. The light shutter of the present invention provides a self contained unit which can be inserted in a standard sized lens aperture in a helmet or goggle assembly. Moreover, the switching mechanism for powering the light shutter on and off is an integral part of the light shutter frame assembly. The light shutter can be easily activated, as a result, from the outside of the helmet or goggle assembly.

The present invention need not be used with other custom components and does not require alteration or modification of the helmet, goggles, or the like, or the alteration of other standard components or parts. Exemplary uses of the present invention include welding helmets, spectacles, goggles, and the like, as well as satiety goggles for nuclear flash protection, for protection from hazards experienced by electric utility workers and for workers at furnace and electrical plant areas and at other places where bright light that could present a risk of injury may occur.

The light shutter of the present invention may be used in a variety of embodiments and applications. The shutter is adjustable to control light, i.e., to increase or to decrease the amount of the incident light which is transmitted through the shutter. When welding is not occurring, for example, the shutter in a welding helmet may be substantially optically clear or transmissive or at least minimizes its attenuation of light. When welding is occurring, the shutter may be dark or closed to reduce the amount of light transmitted therethrough in order to protect the eyes of the person per/brining the welding and maximize his or her viewing comfort. In both cases, though, the image characteristics of the light preferably remain intact. A photosensitive device may be used to sense the intensity of light impinging in the area of the shutter so as to provide an input to a drive circuit for the shutter in order to control opening and closing thereof.

According to one particular aspect of the invention, a frame assembly for a light shutter is provided which comprises a frame structure for enclosing an electro-optic shutter assembly, the frame structure having a front surface which can be positioned opposite a cover lens; and switching means for controlling an operation mode of the electro-optic shutter assembly, the switching means being mounted on said front surface whereby pressure applied to the cover lens activates the :;witching means.

A frame assembly for a light shutter is also provided which comprises a frame structure for enclosing an electro-optic shutter assembly, the frame structure having a top and bottom member joined by a pair of side members for securing the electro-optic shutter assembly; at least one of the top, bottom and side members including housing means for housing a driver circuit for driving the electro-optic shutter assembly; and wherein the housing means comprises a protruding portion of at least one of the top, bottom and side members, said protruding portion extending into an optical area of said shutter.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be suitably employed.

DETAILED DESCRIPTION

Figure 1:
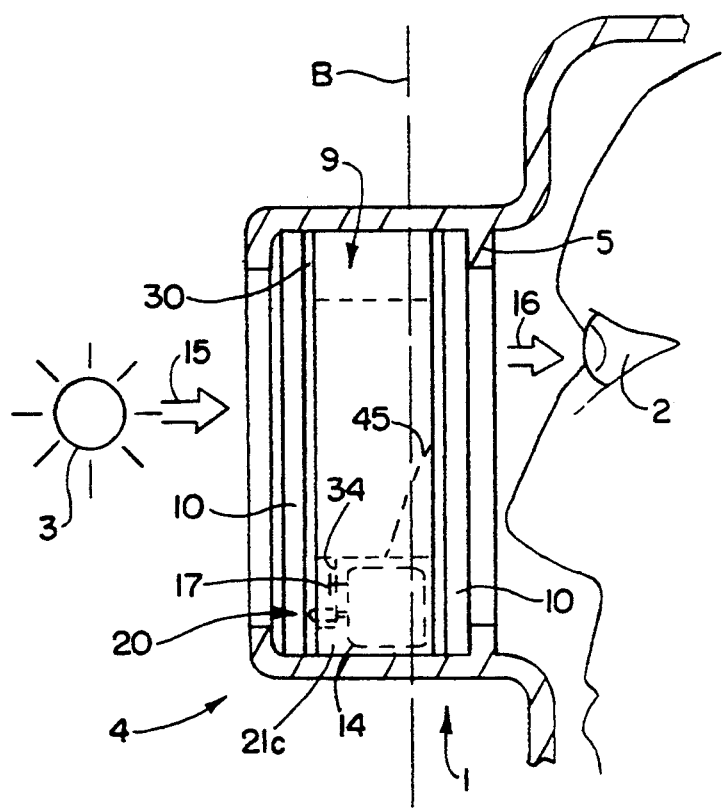
FIG. 1 is a schematic diagram of an electro-optic light shutter and frame assembly used in a welding helmet in accordance with one example of the present invention.

Referring now in detail to the drawings, wherein like reference numerals designate like parts in the several figures, and initially to FIG. 1, a welding helmet 1 (or other protective eye gear) for wearing on the head of a person to protect the eyes 2 of a person from bright light emitted by a welding process, for example, represented as light source 3 is illustrated. Mounted in an aperture 4 and secured by a mounting mechanism 5 is an exemplary electro-optic light shutter and frame assembly 9. The light shutter and frame assembly 9 is sandwiched between a pair of cover lenses 10 which protect the user's eyes 2 and the light shutter and frame assembly 9 from debris, selected wavelengths of light, etc. Preferably, the aperture 4 and the cover lenses 10 are standard sized as is discussed above. The light shutter and frame assembly 9 preferably is rectangular in shape and has a length L dimension and width W dimension (FIG. 2) substantially similar to that of the cover lenses 10 and aperture 4. As a result, the light shutter and frame assembly 9 can be inserted and used in a welding helmet 1 having a standard size lens aperture 4 and standard size cover lenses.

Figure 3:
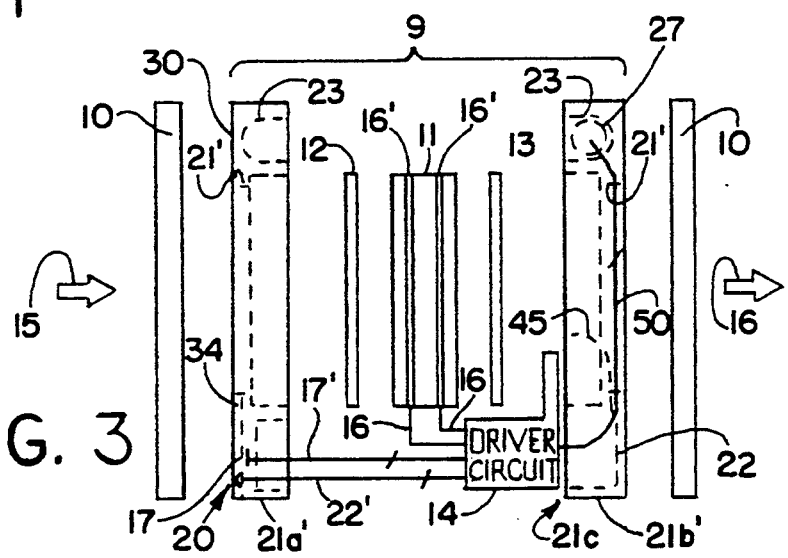
FIG. 3 is a system view of the electro-optic light shutter and frame assembly in accordance with the present invention.

Referring now to FIG. 3, the light shutter and frame assembly 9 includes one or more variable optical retarders 11 (each preferably) sandwiched between a pair of linear polarizers 12, 13. The optical axes of the polarizers 12, 13 may be at right angles to each other and at 45 degrees to the optical axis of the retarder 11 as is described in the above-mentioned patents and patent applications. The retarder 11 may be of the type disclosed in the above-mentioned patents and patent applications. Other types variable retarders also may be used. Other alignments of the components also may be employed, as may be desired to obtain the desirable operation of the shutter 9. If desired, more than one retarder may be used and more than one pair of polarizers may be used.

Further, various other optical components, such as quarter wave plates, compensators, filters, devices to prevent scratching or to block dirt from the other components, etc., can be used in the shutter 9. Moreover, it will be appreciated that one or more of the cover lenses 10 can function as one of the optical components without departing from the scope of the invention. Non-limiting examples of the above-mentioned parts are described in the above-mentioned patents and patent applications.

The light shutter and frame assembly 9 further includes a driver circuit 14 which is operative to provide an electric field of prescribed voltage across the retarder 11 to determine how much of the input light 15 is transmitted as output light 16 by the shutter and frame assembly 9. The driver circuit 14 includes electronic circuitry of conventional design and is connected via lines 16 to transparent electrodes 16' on opposite sides of the retarder 11.

A photosensitive detector 17, for example, in the form of a photosensor arrangement, such as one or more silicon photodetectors (although other photosensors may be used), detects the intensity of the incident light 15 and provides a control input to the driver circuit 14 via line 17' which automatically operates the shutter 9 by applying an appropriate voltage to the retarder 11. An exemplary detector 17 including redundant photosensors and associated circuitry is disclosed in the above patent application. Accordingly, when welding is not detected by the; driver circuit 14 based on the signal line 17', input light 15 is at relatively low intensity, and substantially all of the light possible will be transmitted by the shutter 9 as output light 16. When the driver circuit 14 detects welding based on the signal on line 17', the input light 15 is at a relatively high intensity. Accordingly, the shutter 9 is operative to limit the amount of output light 16.

It will be appreciated that a variety of photosensitive detectors 17 and associated circuitry may be used in connection with the driver circuit 14 and liquid crystal shutter 9 in addition to that which is described herein. It also will be appreciated that other types of detectors or sensors may be employed to provide an input or to provide information to the driver circuit 14 to cause appropriate operation of the light shutter 9. Examples are electrical sensors which sense the electrical energy used to undertake welding and temperature sensors that may be used to sense the change in temperature due to welding. Another sensor would be a flow sensor that detects the flow of a gas used during a welding process. Other types of sensors also may be used, as will be appreciated to those having ordinary skill in the art.

The retarder 11, polarizers 12 and 13, and electrodes 16' are sandwiched together and are secured in stacked relation by a frame assembly 21 portion of the light shutter 9 as is schematically illustrated in FIG. 3. The frame assembly 21 in the exemplary embodiment includes halves 21a' and 21b' which are designed to receive and maintain in fixed relation the retarder 11, polarizers 12 and 13, and electrodes 16'. The frame assembly 21 has an aperture 21' through which the input light 15 can be selectively transmitted/blocked by the retarder 11. etc. The frame assembly 21 also includes a housing portion 22 for enclosing the driver circuit 14 for driving the retarder 11. The driver circuit 14 may consist of, for example, an integrated circuit or discrete components mounted on a printed circuit board (not shown). The frame assembly 21 further includes a housing portion 23 which is used to enclose a battery 27 or the like which provides electrical power to the driver circuit 14.

The frame assembly 21 has a front surface 30 which is at least partially exposed on the outside of the welding helmet 1 via the welding helmet lens aperture 4. The front surface 30 includes a recessed surface 34 having a depth D (FIG. 4A) in which the photosensitive detector 17 is mounted. A switching mechanism 20 is mounted in the recessed surface 34. The switching mechanism 20 allows the user to turn power to the light shutter on and off from the outside of the welding helmet 1 as is further described below.

Figure 2:
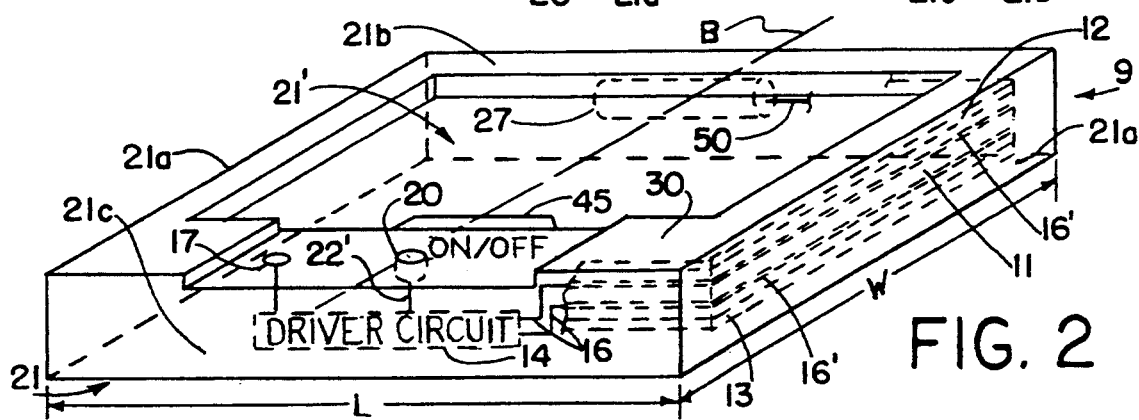
FIG. 2 is an isometric view of the electro-optic light shutter and frame assembly of FIG. 1 in accordance with the present invention.

It will be appreciated that the light shutter and frame assembly 9 as shown in FIG. 3 is not shown to scale in order to illustrate and to identify the various elements thereof most clearly. When the light shutter and frame assembly 9 is fully assembled as is shown in FIG. 2, the light shutter and frame assembly 9 forms an integrated unit. The frame assembly 21 secures the edges of the retarder 11, polarizers 12, 13, etc., and encloses the driver circuit 14 and battery 27. The light shutter and frame assembly can therefore easily be sandwiched between the cover lenses 10 and inserted in the helmet lens aperture 4. Because the mounting mechanism 5 is removable, as is conventional, the light shutter and frame assembly 9 can be removed and the cover lens(es) 10 replaced or changed quickly and easily using standard size lenses.

The frame assembly 21 can be made of any number of conventional materials, but preferably is made of a lightweight, impact resistant plastic. The frame assembly 21 can be manufactured using any number of conventional techniques such as injection molding, milling, etc. The length L and width W dimensions of the frame assembly 21 preferably are the same as those of a standard cover lens with which it is used such as the cover lens mentioned above. The respective dimensions of the housing portions 22 and 23 will be a function of the size of the corresponding driver circuit 14 and battery 27 as will be appreciated. Preferably, however, the size of the housing portions 22, 23 is minimized in order to maximize the amount of actual viewing area through the aperture 21 in the light shutter 9. Also, it will be appreciated that although the frame assembly 21 is described herein as completely enclosing the outer perimeter of the light shutter retarder 11, polarizers, etc., the frame assembly 21 may only partially enclose the various electro-optic components. The frame assembly 21 as referred to herein is intended to encompass any portion of the light shutter and frame assembly 9, and more preferably a portion which is not intended to provide directly an optical function such as blocking, polarizing, rotating, etc., incident light.

As is mentioned above, the driver circuit 14 includes a switching mechanism 20 mounted at the recessed surface 34 of the frame 21. The switching mechanism 20 can be almost any type of switch such as a mechanical contact switch, a capacitance switch, a micro-switch, etc., which is connected to the driver circuit 14 by lines 22'. In the exemplary embodiment, the position or state of the switching mechanism 20 determines the power on/off state of the light shutter 9 having conventional power on/off capabilities. In other words, when the welder wants to use the welding helmet 1, the switching mechanism 20 is used to turn the light shutter 9 "on" so that power from the battery 27 or the like energizes the driver circuit 14 via lines 50. When the welder wishes to deactivate the welding helmet 1, the switching mechanism 20 is used to turn the light shutter 9 "off" whereby the power from the battery 27 no longer energizes the driver circuit 14 and battery power is conserved.

In another embodiment, the switching mechanism 20 can be used to switch the driver circuit 14 between operational modes other than simply "on" and "off". For example, the position or state of the switching mechanism 20 can be used to determine whether the driver circuit 14 is operative for intermittent-type welding mode or for continuous type welding. Alternatively, the switching mechanism 20 can be used to switch or change the type of optical filtering provided by the light shutter. For example, the switching mechanism 20 may be used to enable/disable one or more additional retarders 11 enclosed within the frame 21. The switching mechanism 20 also can be used to determine the darkness of the light shutter. Various other types of switching of operational modes of the driver circuit 14 will be readily apparent to someone of ordinary skill in the art in view of the present disclosure. The specific modes between which the switching mechanism 20 is used to switch is not crucial to the invention, as will be appreciated. The present invention is intended to encompass any and all such variations.

Figure 4A:
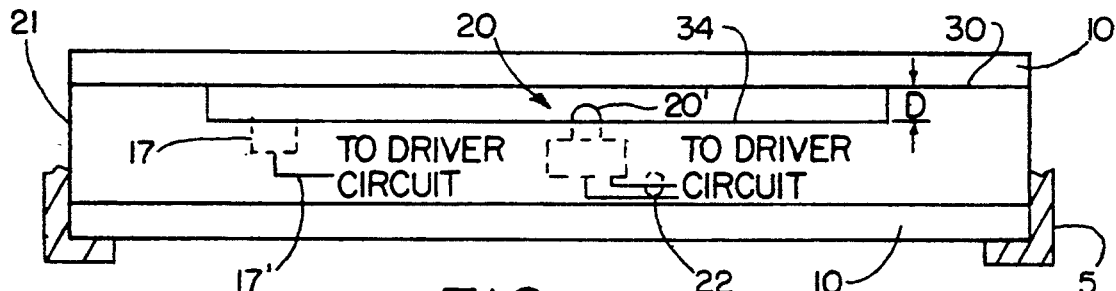
FIG. 4A is a partial bottom view of the electro-optic light shutter and frame assembly in accordance with the present invention.
Figure 4B:
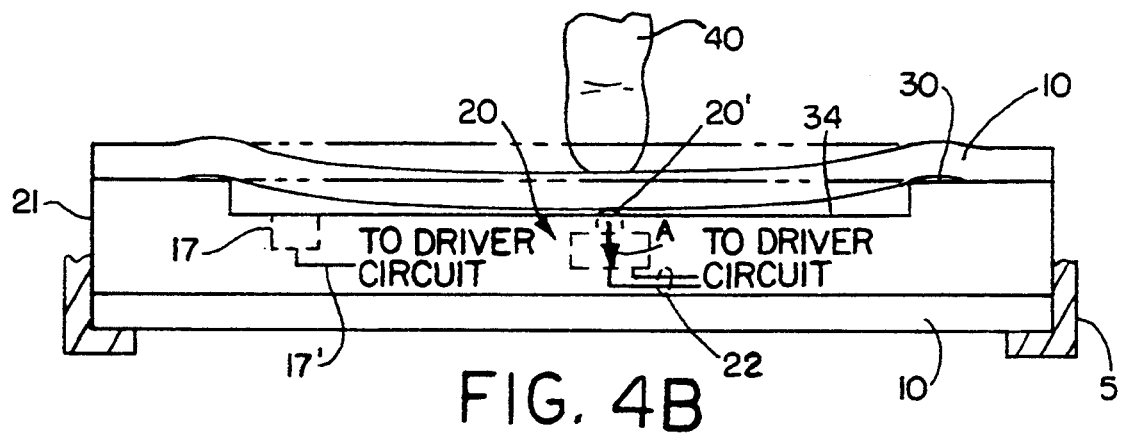
FIG. 4B is a partial bottom view of the electro-optic light shutter and frame assembly of the present invention with the cover lens flexed to active the switching mechanism.

Referring now to FIG. 4A, the switching mechanism 20 will be described in more detail. The switching mechanism 20 is mounted in the frame assembly 21 at the recessed surface 34. In one embodiment the switching mechanism 20 is a contact type switch having a mechanical plunger element 20'. At least a portion of the plunger element 20' extends beyond the recessed surface 34 towards the adjacent cover lens 10. The cover lens 10 is known to have a certain degree of flexibility. The extent of such flexibility is a function of the thickness of the cover lens 10 and the type of material of which the cover lens is made. For example, plastic and polycarbonate lenses are known to have a substantial degree of flexibility. Accordingly, when the user exerts pressure on the cover lens 10 in the area of the switching mechanism 20 with a finger 40 or the like from the outside of the helmet 1, the cover lens 10 will flex inward so that the plunger element 20' is depressed in the direction of arrow A as is shown in FIG. 4B. By depressing the plunger element 20', the state of the switching mechanism 20 is changed as is conventional with plunger type switches. As a result, the state of the switching mechanism 20 can be changed simply by exerting a small amount of pressure on the cover lens 10.

There are numerous advantages associated with the switching aspects of the present invention. The user can quickly and easily turn power to the light shutter 9 on and off from outside the helmet 1, for example, simply by pressing the cover lens 10 in order to activate the switching mechanism 20. Because the cover lens 10 completely covers the light shutter and frame assembly 9, the cover lens 10 continues to protect the entire light shutter and frame assembly 9 from din and debris. It is not necessary that the switching mechanism 20 be exposed to the welding environment or remain on the inside the welding helmet 1 as with conventional light shutters. Moreover, the cover lens 10 can be a standard size and type cover lens and is easily replaceable.

It will be appreciated that the depth D (FIG. 4A) of the recessed surface 34 will depend on the requirements of the switching mechanism 20. For example, commercially available switches require plunger movement as little as thirty thousandths of an inch. Thus, the depth D of the recessed surface 34 is preferably approximately that of the required plunger movement so that the cover lens 10 can flex relatively freely to depress the plunger element 20' and the switching mechanism 20 can be activated. Various cover lenses 10 can be used in accordance with the present invention so as to provide sufficient flexing to enable the user to activate the switching mechanism 20 in accordance with the present invention. For example, commercially available standard lenses made of plastic, polycarbonate material, resin, etc. are available (such as the lens identified above) which include the desired degree of flexibility.

Figure 5:
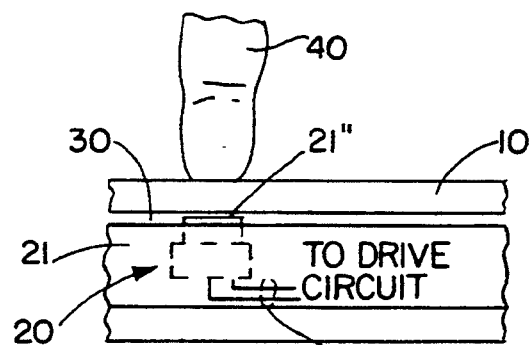
FIG. 5 is a partial bottom view of the electro-optic light shutter and frame assembly according to another embodiment of the present invention.

Referring now to FIG. 5, another embodiment of the invention is shown with respect to the switching mechanism 20. In this embodiment, a pressure-sensitive type switching mechanism 20 is utilized in place of the above-described plunger-type switching mechanism. As is conventional, the pressure-sensitive type switching mechanism 20 detects a change in pressure applied to the switch and delivers a corresponding signal via line 22' to the driver circuit 14. As a result, the driver circuit can be powered on and off as is discussed above. In this embodiment the cover lens 10 is shown directly adjacent the front surface 30 in which the pressure sensitive switching mechanism 20 is mounted. Because the switching mechanism 20 detects a change in applied pressure on surface 21", it is not necessary that a recessed surface 34 be provided in order to activate the switching mechanism 20. Furthermore, it will be appreciated that the recessed surface 34 is not a necessary part of the invention, but rather is included only as part of one of the preferred embodiments. For example, in another embodiment in which a switching mechanism 20 having a mechanical plunger element 20' is used, a spacer (not shown) can be inserted between the front surface 30 of the frame assembly 21 and the adjacent cover lens 10 in order to provide the appropriate amount of area for movement of the flexible cover lens 10 in order to activate the switching mechanism 20.

Furthermore, it will be appreciated that in an embodiment such as that shown in FIG. 5 where the switching mechanism 20 requires little or no mechanical movement, the flexing requirements of the adjacent cover lens 10 are minimal.

In still another embodiment of the present invention, a capacitance-type switch can be used as the switching mechanism 20 and can be mounted on the front surface 30 of the frame assembly 21 in the same manner shown in FIG. 5. By touching the cover lens 10 in the area of the switching mechanism 20, the cover lens 10 comes in contact with and/or the related touching alters the capacitance of the capacitance-type switch in order to activate the switching mechanism.

Various other types of switches can be used with the invention including microswitches, mechanical switches, electro-mechanical switches, etc.

Even further, a pneumatic or hydraulic type switching mechanism 20 can be used. For example, the switching mechanism 20 can include a bellows mounted on the recessed surface 34. The line 22' represents a small hydraulic or pneumatic hose coupled between the bellows and a pressure sensor in the driver circuit 14.

In each of the above-described embodiments, the user is able to activate the switching mechanism 20 by way of applying pressure to the cover lens 10 from outside the welding helmet or other protective eye gear. Thus, the user is able to quickly and easily alter the operational mode of the light shutter and frame assembly 9. At the same time, the cover lens 10 provides protection to the light shutter from debris, etc., as well as operating as a protective filter if desired.

Referring again to FIGS. 1 and 2, the light shutter and frame assembly 9 in the preferred embodiment has the switching mechanism 20 located on the front surface 30 of the frame assembly 21 along a vertical axis B. The axis B is centered horizontally along the face of the welding helmet 1. As a result, pressure applied to the cover lens 10 in order to activate the switching mechanism 20 is applied along the center of the face of the welding helmet 1. Thus, the welding helmet 1 is less likely to become skewed on the head of the user as may happen if pressure is to be applied to the cover lens 10 in an area off the horizontal center of the welding helmet 1 as will be appreciated.

Referring again specifically to FIG. 2, the frame assembly 21 is constructed of a pair side members 21a joined by top and bottom members 21b and 21c, respectively. The top, bottom and side members form the outer perimeter of the aperture 21' of the light shutter and frame assembly 9 as is shown. In the preferred embodiment, the bottom member 21C includes a protruding portion 45 which is positioned along the vertical axis B. Preferably, the protruding portion 45 forms part of the housing portion 22 which houses the driver circuit 14.

The protruding portion 45 is preferably located directly adjacent the crest of the nose of the user when installed in the welding helmet 1 or other protective eye gear. As a result, the protruding portion 45 provides a means for enclosing the driver circuit 14 or related circuitry if necessary while sacrificing as little viewing area of the aperture 21' as possible. Thus, even if the driver circuit 14 is relatively large in size, the frame assembly 21 maximizes the viewing area by enclosing the driver circuit 14 at least partially using the protruding portion 45 in an area which is less critical with respect to viewing, such as directly in front of the crest of the nose.

There may be instances where it is important that the user have full-viewing capability through the aperture 21' at least with respect to when the user is looking sharply downward through the light shutter and frame assembly 9. Another advantage of the present invention is that the light shutter and frame assembly 9 can be easily removed from the welding helmet 1 and rotated 180° so that the protruding portion 45 then effectively becomes part of the top member (i.e., 2 lb.). Such capabilities of the present invention are particularly due to the symmetry of the frame assembly 21 and the fact that the frame assembly 21 fits easily within a standard sized aperture 4, such rotation of the light shutter and frame assembly 9 is both easy and convenient.

Although the invention has been shown and described with respect to certain preferred embodiments, it is obvious that equivalents and modifications will occur to others skilled in the art upon the reading and understanding of the specification. The present invention includes all such equivalents and modifications, and is limited only by the scope of the following claims.

What is claimed is:

1. A frame assembly for a light shutter, comprising:
  a frame structure for enclosing an electro-optic shutter assembly, said frame structure having a front surface which can be positioned opposite a cover lens; and
  switching means for controlling an operation mode of said electro-optic shutter assembly, said switching means being mounted on said front surface whereby pressure applied to said cover lens activates said switching means.

2. The frame assembly of claim 1, said front surface comprising a recess area on which said switching means is mounted.

3. The frame assembly of claim 2, wherein said pressure is applied opposite said recess area.

4. The frame assembly of claim 3, wherein said pressure causes said cover lens to flex and thereby activate said switching means.

5. The frame assembly of claim 4, wherein said switching means comprises a contact switch, and said cover lens activates said contact switch by coming into contact with said contact switch.

6. The frame assembly of claim 4, wherein said switching means comprises a micro-switch, and said cover lens activates said micro-switch by coming into contact with said micro-switch.

7. The frame assembly of claim 4, wherein said switching means comprises a capacitive switch, and ,said cover lens activates said capacitive switch by coming into contact with said capacitive switch.

8. The frame assembly of claim 1, wherein said switching means comprises a switch selected from the group consisting of a contact switch, a micro-switch, and a capacitive switch.

9. A welding helmet including the frame assembly of claim 1, said welding helmet further including said cover lens whereby said cover lens is positioned between said frame assembly and the outside of said welding helmet.

10. The welding helmet of claim 9, wherein said switching means controls whether said electro-optic shutter assembly is in a power on condition or a power off condition.

11. The welding helmet of claim 9, said front surface comprising a recess area on which said switching means is mounted.

12. The welding helmet of claim 11, wherein said pressure is applied opposite said recess area.

13. The welding helmet of claim 12, wherein said pressure causes said cover lens to flex and thereby activate said switching means.

14. The welding helmet of claim 9, wherein said frame structure fits within a standard size welding helmet lens aperture.

15. The welding helmet of claim 14, wherein said cover lens is a standard size cover lens corresponding to said standard size welding helmet lens aperture.

16. The welding helmet of claim 15, wherein said cover lens is operative to protect said electro-optic shutter assembly from damage.

17. The welding helmet of claim 16, wherein said cover lens is further operative to protect said frame structure from damage.

18. The welding helmet of claim 9, wherein said switching means is positioned on said front surface along a horizontal center of the face of said welding helmet.

19. The frame assembly of claim 1, said frame structure further comprising housing means for housing a driver circuit intended to drive said electro-optic shutter assembly.

20. The frame assembly of claim 19, wherein said switching means controls whether said driver circuit is in a power on condition or a power off condition.

21. The frame assembly of claim 20, said frame structure further comprising additional housing means for housing a battery for powering said driver circuit.

22. A frame assembly for a light shutter, comprising:
a frame structure for enclosing an electro-optic shutter assembly, said frame structure having a top and bottom member joined by a pair of side members for securing said electro-optic shutter assembly; at least one of said top, bottom and side members including housing means for housing a driver circuit for driving said electro-optic shutter assembly; and wherein said housing means comprises a protruding portion of said at least one of said top, bottom and side members, said protruding portion extending into an optical area of said shutter.

23. The frame assembly of claim 22, wherein said protruding portion is for housing electrical circuitry associated with said driver circuit.

24. The frame assembly of claim 23, further comprising another housing means for housing a power source for powering said driver circuit.

25. An eye protection system including the frame assembly of claim 23, wherein said protruding portion is positioned in a substantially non-viewing area relative to the user.

26. The eye protection system of claim 25, wherein said protruding portion is positioned substantially near the crest of the nose of the user.

27. The eye protection system of claim 25, said eye protection system being part of a welding helmet.

28. The eye protection system of claim 27, wherein said frame structure fits within a standard size welding helmet lens aperture.

29. The eye protection system of claim 27, said frame structure being sized to fit in a lens aperture of said welding helmet in at least two different positions whereby a user can position said protruding portion to a preselected non-viewing area.

30. A frame assembly for a light shutter in a welding helmet, comprising:
a frame structure for an electro-optic shutter assembly, said frame structure having a front surface to be exposed to light associated with a welding operation; and
switching means for controlling an opt, rational mode of said electro-optic shutter assembly, said switching means being mounted on said front surface.

31. The frame assembly of claim 30, said front surface comprising a recess area on which said switching means is mounted.

32. The frame assembly of claim 31, wherein said switch means is a pressure responsive switch positioned to respond to pressure applied to said switching means to activate said switching means via said front of said frame structure.

33. The frame assembly of claim 1, wherein said switching means comprises a switch selected from a group consisting of a contact switch, a micro-switch, and a capacitive switch.

34. A frame assembly for a light shutter for eye protection, comprising:
a frame structure for an electro-optic shutter assembly, said frame structure having a front intended to face a source of bright light through a cover lens and a rear intended to face toward the face of a person, and
switching means for controlling an operational mode of said electro-optic shutter assembly, said switching means being positioned relative to said frame structure for activation from said front of said frame structure as a result of pressure applied to said cover lens.

* * * * *